(12) United States Patent
Maccariello et al.

(10) Patent No.: US 11,471,350 B2
(45) Date of Patent: Oct. 18, 2022

(54) CONSTRUCTIVE LAYOUT IN CONTAINER

(71) Applicants: Elizabeth Regina Maccariello, Rio De Janeiro (BR); Eduardo Rocha, Rio De Janeiro (BR); Alessandra Cananéa De Sá Teixeira, Rio De Janeiro (BR); Guilherme Henrique Do Amaral Silva, São Paulo (BR); Indalecio Villar Junior, São Paulo (BR); Leandro Siqueira Armani, São Paulo (BR)

(72) Inventors: Elizabeth Regina Maccariello, Rio De Janeiro (BR); Eduardo Rocha, Rio De Janeiro (BR); Alessandra Cananéa De Sá Teixeira, Rio De Janeiro (BR); Guilherme Henrique Do Amaral Silva, São Paulo (BR); Indalecio Villar Junior, São Paulo (BR); Leandro Siqueira Armani, São Paulo (BR)

( * ) Notice: Subject to any disclaimer, the term of this patent is extended or adjusted under 35 U.S.C. 154(b) by 311 days.

(21) Appl. No.: 16/639,666

(22) PCT Filed: Jan. 29, 2018

(86) PCT No.: PCT/BR2018/000002
§ 371 (c)(1),
(2) Date: Feb. 17, 2020

(87) PCT Pub. No.: WO2019/119081
PCT Pub. Date: Jun. 27, 2019

(65) Prior Publication Data
US 2020/0170865 A1    Jun. 4, 2020

(30) Foreign Application Priority Data
Dec. 21, 2017 (BR) .......................... 2020170277319

(51) Int. Cl.
  *A61G 10/02* (2006.01)
  *A61B 50/10* (2016.01)
  (Continued)

(52) U.S. Cl.
  CPC .............. *A61G 10/02* (2013.01); *A61B 50/10* (2016.02); *A61B 90/37* (2016.02); *B01L 1/04* (2013.01);
  (Continued)

(58) Field of Classification Search
  CPC ........ A61G 10/02; A61B 50/10; A61B 90/37; A61B 2050/105; A61B 2090/309;
  (Continued)

(56) References Cited

U.S. PATENT DOCUMENTS

| 5,656,491 A | 8/1997 | Cassani et al. |
| 2002/0189173 A1* | 12/2002 | Staschik ................... F24H 1/08 52/79.1 |

(Continued)

FOREIGN PATENT DOCUMENTS

| BR | PI0709832 A2 | 7/2011 |
| CN | 202913719 U | 5/2013 |

(Continued)

OTHER PUBLICATIONS

International Search Report for corresponding PCT/BR2018/00002.
Written Opinion of the ISA for corresponding PCT/BR2018/00002.

*Primary Examiner* — Gisele D Ford
(74) *Attorney, Agent, or Firm* — Egbert, McDaniel & Swartz, PLLC

(57) ABSTRACT

Constructive layout in a container, to provide clean areas for medical and hospital care, such as fractionation of solid and liquid oral drugs (ISO8) and handling of sterile drugs (ISO7), as well as the configuration of the containers for the infusion, diagnosis, surgery, ICU and hemodialysis areas.

15 Claims, 3 Drawing Sheets

(51) Int. Cl.
*A61B 90/00* (2016.01)
*B01L 1/04* (2006.01)
*E04B 1/343* (2006.01)
*E04H 1/12* (2006.01)
*E04H 3/08* (2006.01)
*A61B 90/30* (2016.01)
*A61B 5/00* (2006.01)
*A61M 1/14* (2006.01)
*A61M 5/14* (2006.01)

(52) U.S. Cl.
CPC ....... *E04B 1/34336* (2013.01); *E04H 1/1205* (2013.01); *E04H 3/08* (2013.01); *A61B 5/6889* (2013.01); *A61B 2050/105* (2016.02); *A61B 2090/309* (2016.02); *A61B 2505/03* (2013.01); *A61B 2505/05* (2013.01); *A61M 1/14* (2013.01); *A61M 5/14* (2013.01); *B01L 2300/12* (2013.01); *B01L 2300/16* (2013.01); *E04H 2001/1283* (2013.01)

(58) Field of Classification Search
CPC ............. A61B 5/6889; A61B 2505/03; A61B 2505/05; B01L 1/04; B01L 2300/12; B01L 2300/16; E04B 1/34336; E04H 1/1205; E04H 3/08; E04H 2001/1283; A61M 1/14; A61M 5/14

See application file for complete search history.

(56) References Cited

U.S. PATENT DOCUMENTS

| | | | |
|---|---|---|---|
| 2004/0025448 | A1* | 2/2004 | Puusepp .................. G21F 3/00 52/64 |
| 2005/0193643 | A1* | 9/2005 | Pettus .................... F24F 3/167 52/79.1 |
| 2005/0218075 | A1 | 10/2005 | Graetz et al. |
| 2007/0132262 | A1* | 6/2007 | Chui Peng Sun ..... A61G 3/001 296/24.38 |
| 2011/0041415 | A1* | 2/2011 | Esposito ............... E04H 1/1205 52/12 |
| 2012/0077429 | A1 | 3/2012 | Wernimont et al. |
| 2016/0010883 | A1* | 1/2016 | Jornitz .................... F24F 13/32 29/897.3 |
| 2017/0030097 | A1* | 2/2017 | Marinoni ................ E04H 5/02 |
| 2017/0130447 | A1* | 5/2017 | Lane, Jr. .............. A61G 3/0858 |
| 2018/0230690 | A1* | 8/2018 | Leibinger ............. E04B 1/3483 |

FOREIGN PATENT DOCUMENTS

| | | |
|---|---|---|
| CN | 204370850 U | 6/2015 |
| EP | 0670889 B1 | 9/1995 |
| EP | 2007953 A1 | 12/2008 |
| WO | 2015079273 A1 | 6/2015 |

* cited by examiner

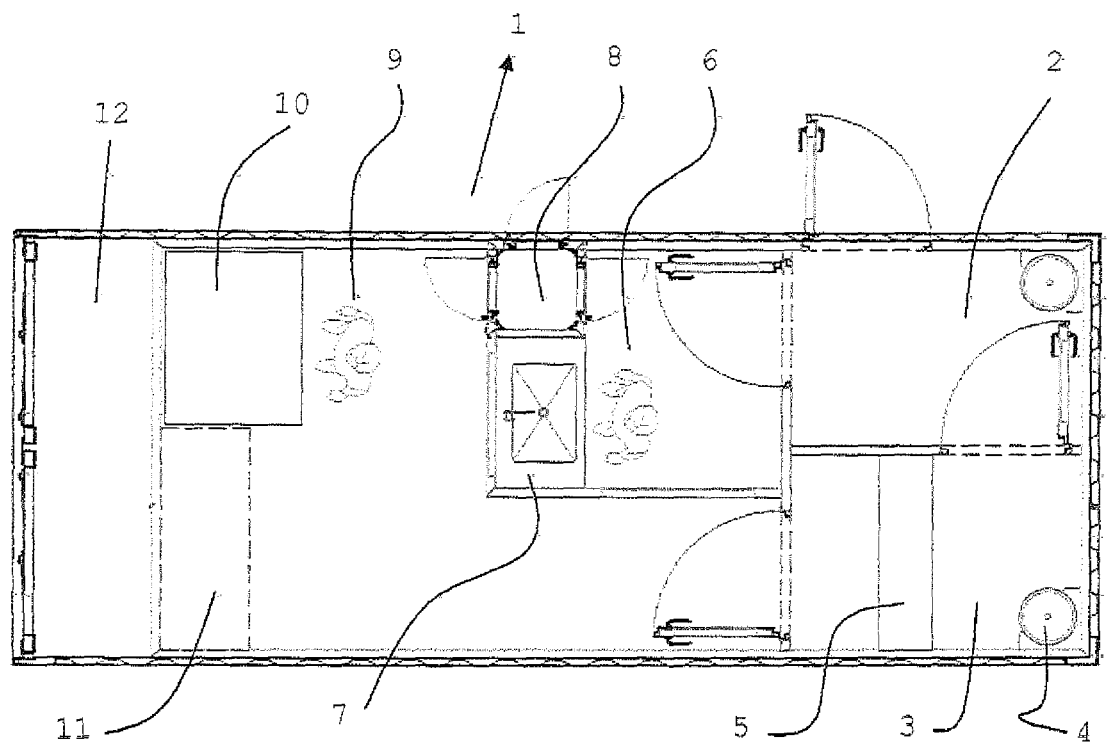
FIGURE 1.1
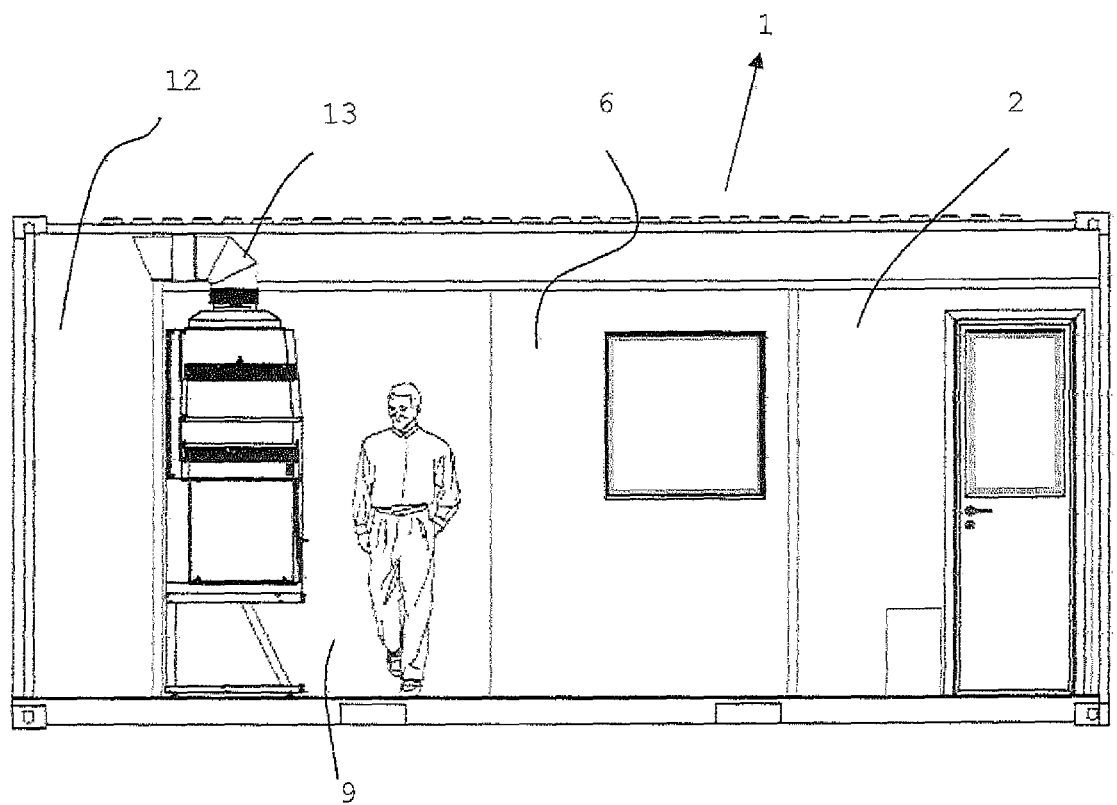
FIGURE 1.2

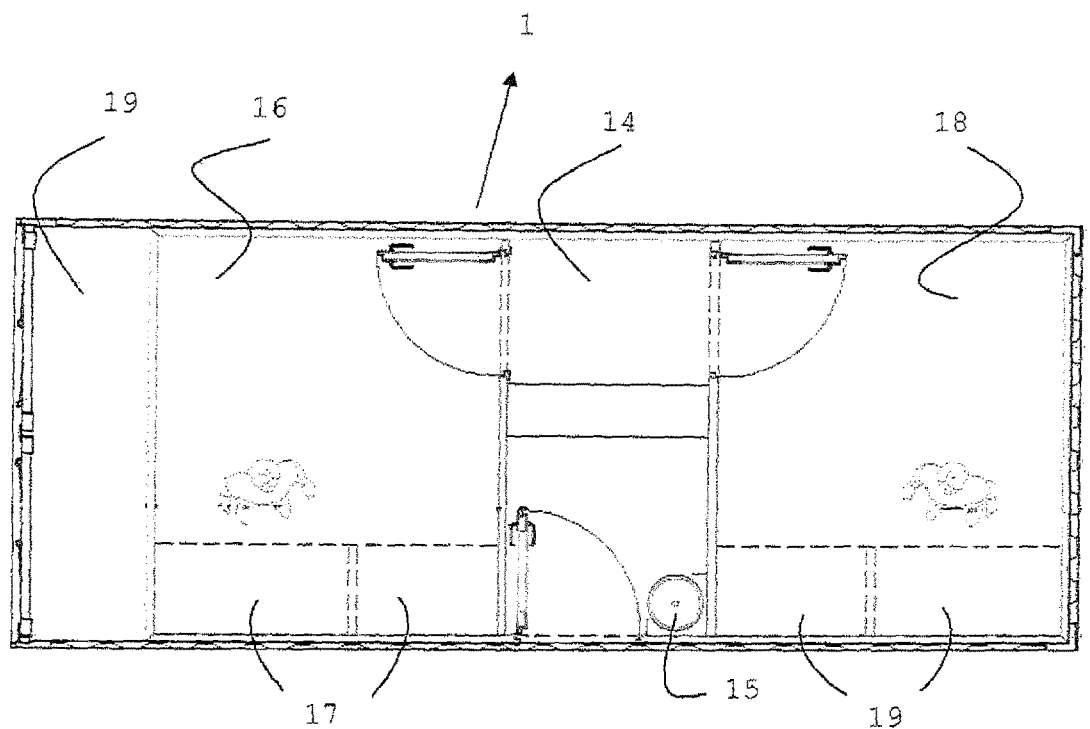
FIGURE 2.1
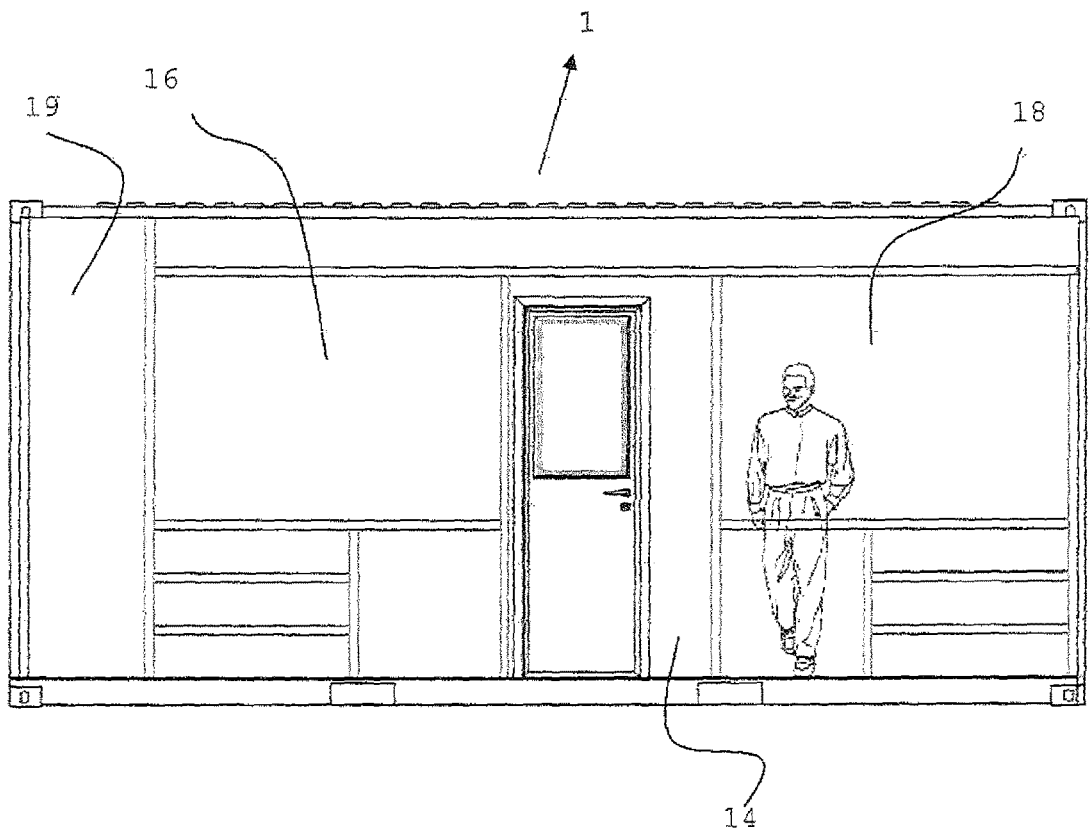
FIGURE 2.2

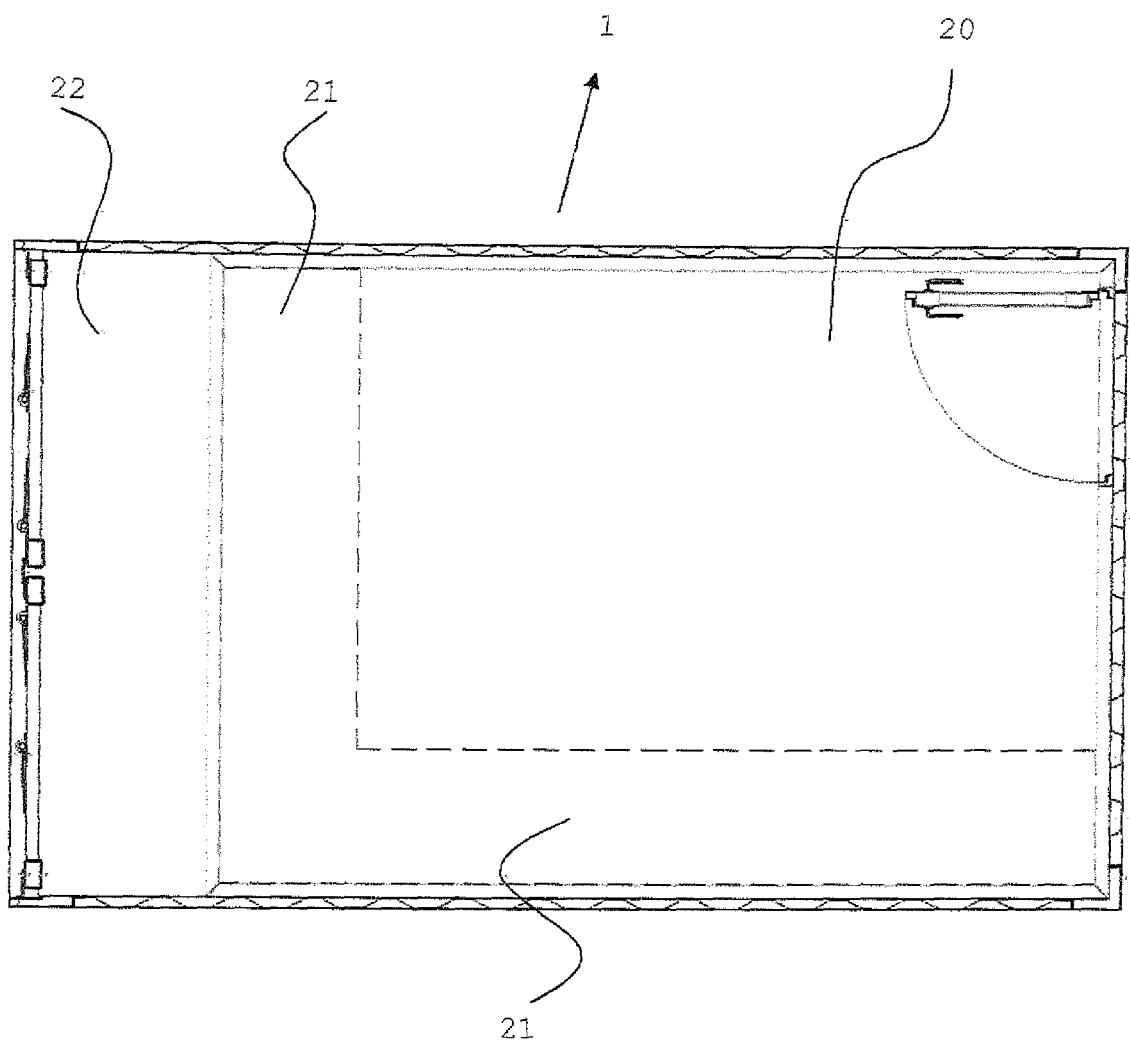
FIGURE 3.1

CONSTRUCTIVE LAYOUT IN CONTAINER

FIELD OF APPLICATION

The present utility model refers to the field of medical-hospital treatment and biosafety units, specifically to a mobile, modular clean room, more specifically, to a container equipped with a complete autonomous clean room structure for drug handling and medical treatment.

PRIOR ART AND EXISTING PROBLEMS

The American patent U.S. Pat. No. 5,656,491 granted for Cassani et al. teaches, briefly, the installation of mobile modules for the preparation of biotechnological products on a pilot scale, comprising equipment for the production, separation, purification and finishing of the products. The installation consists of at least two mobile modules suitable for being connected together and integrated one with the other.

The American patent US2012007429 granted for Wernimont et al. refers, briefly, to a clean room made up of pre-assembled modules. The first pre-assembled module includes an air filtration system with a ceiling chamber to provide clean air to the interior of the module. The system is transported and delivered in its pre-assembled form.

Patent PI0709832-4 granted for Vladimir Grcevic, reveals, briefly, a laboratory consisting of antechambers for the analysis of consistent pathogenic agents in a transportable mobile container containing a base chamber isolated from the outside by a watertight box inserted in said chamber. The box equipped with a pressure device to allow maintenance of the negative pressure relative to the external environment. Said watertight box comprising a first antechamber of the protection equipment, a second antechamber communicating with the pathogenic agents' analysis zone and a third antechamber communicating with the analysis zone and the first antechamber.

Several mobile clean rooms are known. However, mobile clean rooms specifically designed for hospital application are not found among the available solutions.

As is well known to those skilled in the art, hospitals use clean rooms for the handling of all injectable, such as individualized solutions for intravenous infusion (IV), fractionation of intravenous antibiotics, fractionation of chemotherapy doses and biopharmaceuticals, production of individualized dialysis solutions and parenteral or enteral nutrition.

A remaining problem refers to the fact that the lack of clean area for handling drugs often prevents the treatment of a more complex patient in hospital units or advanced health clinics; in the case of relying on bedside manipulation, there is an added risk of contamination and error of dose fractionation and it may also expose the handler to the risk of toxic substances; if the hospital unit chooses to outsource manipulation, the high cost, displacement and proximity of urban centers are issues to be considered.

All clean-area pharmacies are built according to the client's physical space and planned demand. Its construction is time-consuming (space analysis, adaptation or new construction), fixed, with high construction and maintenance costs, and is not standardized or reproducible (for being created according to the characteristics of the space and conditions of the pharmaceutical industry or hospital unit).

Therefore, it would be highly desirable and advantageous to obtain a mobile hospital clean room, intended for diagnosis, implementation of therapy, specially the handling and dispensing of injectables.

Although some prior art documents report mobile clean rooms, functional parameters achieved by the present model are not found therein.

Model Solution

The present model aims to provide a mobile unit for the provision of a complete and ready for use scalable clean room, with pressure, temperature, humidity and air HVAC control for medical treatment and drug handling, the unit being delivered as equipment, with the whole system installed.

Thus, the unit may be integrated into the existing hospital units as well as be displaced for complex care in poor areas affected by wars, conflicts or disasters.

These and other purposes are achieved by means of a constructive layout applied in a container consisting in the installation of all the equipment suitable for the structuring of the clean area and medical-hospital care.

Novelty and Inventive Step

The layout revealed herein and further detailed, which consists of the application on containers of clean areas for medical-hospital care, such as fractionation of solid and liquid oral drugs (ISO8) and handling of sterile drugs (ISO7), as well as the configuration of the containers for the infusion, diagnosis, surgery, ICU and hemodialysis areas, are not taught by the representative documents of the state of the art relating to the field of application of this model, being uncommon and unusual choices in relation to the normal activity of the technical area. According to the available teachings, technicians are led to erect clean rooms incorporated into the construction and design of hospitals.

Functional Improvement

Applying the form and layout taught herein, the present model provides containers structurally configured as clean rooms of hospitals and therapeutic hospital centers.

Among the advantages of the model are: reduction of the cost and time of manufacture of clean areas; agility in the implantation in existing hospitals and for the care in deprived, conflict or disaster areas; possibility of enlarging or resizing the area of interest by coupling a new container; better use of the patient care intra-hospital area, while the stocking and preparation of the drug can be performed in modules outside the main building.

Another advantage is to provide greater safety for the patient with adequate preparation of the drug doses: reduction of the microbiological contamination risk; lower risk of dose errors; safety for the handler due to the lower risk of contamination with toxic material.

As the unit includes GMP controlled areas and equipment compatible with FDA, ANVISA or equivalent foreign regulatory agencies, another benefit of the model is to meet the hospitals aiming for international quality and safety certification, as they need to implant a unit dose system.

It is also possible to point out as advantage of the model its reproducibility given the standardization of the dean area modules, drug inventory, ICU, surgical center, infusion center, dialysis center.

DESCRIPTION OF THE DRAWINGS

The model is clarified below by its representation in the drawings that show:

FIG. 1.1—top view of the clean handling and washing room (ISO7);

FIG. 1.2—cross-sectional side view of the clean handling (ISO7) and washing (ISO8) room;

FIG. 2.1—top view of the clean fractionation room (ISO8);

FIG. 2.2—cross-sectional side view of the clean fractionation room (ISO8);

FIG. 3.1—top view of a constructive variant of the model for the support/labeling/storage area.

DESCRIPTION OF THE MODEL

FIGS. 1.1 and 1.2 show the constructive embodiment of the layout according to the model applied in container (1) in the constructive form of clean handling and washing room ISO7, intended for handling of injectables, which includes a modular installation of isopanel-coated container or flat partition in sheet steel with thermal and acoustic insulating substrate of polystyrene (EPS) or polyurethane (PUR) or polyisocyanurate (FIR) or rock wool (LDR) or in aluminum wire mesh, the entire interior finished with sanitary rounded profiles (aluminum/PVC/stainless steel or similar) to facilitate cleaning and prevent dirt buildup, vinyl-coated floor with high traffic resistance and resistance against fungi and bacteria, lighting of the rooms will be made through built-in or overlapping luminaires with sealing to the maintenance area, LED lamps, sink drainage system in PVC pipe or similar, sink feeding system in PVC pipe or similar, all doors, displays and accessories in GMP standard, equipped with HVAC system, pressure monitoring, the said modular installation being composed of: primary antechamber (2) (1.63 m$^2$) for people entrance, said primary antechamber containing alcohol gel dispenser, electromagnetic door interlock system by CLP control and cabinet for supplies; gowning antechamber (3) (1.95 m$^2$) for people containing: sink (4) for sanitizing in AISI 304 stainless steel and (sensor driving) high spout faucet, fed by water purified by reverse osmosis system or similar, electromagnetic door interlock system by CLP control, bench (5) with AISI 304 stainless steel coating with storage compartment for gowning, cabinet for storage of supplies and waste for disposal; washing/sterilization room (6) (2.15 m$^2$) containing: washing countertop (7) in AISI 304 stainless steel with lower shelves for storage, fed by water purified by reverse osmosis system or similar, cabinet for storage of supplies and waste for disposal; double pass-through (8) 550×550×1100 mm for material input and output with electromagnetic door interlock system by CLP control; handling area (9) (5.5 m$^2$) containing: II B2 biosecurity cabin (10), workbench (11) with AISI 304 stainless steel on 2 levels; engine room (12) comprising: fan coil (13) with coarse, fine and absolute filtration for air cooling and cleaning, power and control board for electrical supply of the container, automation board of the air conditioning system, interlocking board for doors and pass-throughs, reverse osmosis system.

FIGS. 2.1 and 2.2 show the constructive embodiment of the layout according to the model applied in container (1) in the constructive form of clean room for fractionation area ISO8, which includes a modular installation of isopanel-coated container or flat partition in sheet steel with thermal and acoustic insulating substrate of polystyrene (EPS) or polyurethane (PUR) or polyisocyanurate (PIR) or rock wool (LDR) or in aluminum wire mesh, the entire interior finished with sanitary rounded profiles (aluminum/PVC/stainless steel or similar) to facilitate cleaning and prevent dirt buildup, vinyl-coated floor with high traffic resistance and resistance against fungi and bacteria, lighting of the rooms will be made through built-in or overlapping luminaires with sealing to the maintenance area, LED lamps, sink drainage system in PVC pipe or similar, sink feeding system in PVC pipe or similar, all doors, displays and accessories in GMP standard, equipped with HVAC system, pressure monitoring, the said modular installation being composed of: antechamber (14) (1.71 m$^2$) for people entrance containing: washbasin (15) for sanitizing in AISI 304 stainless steel and high spout faucet, electromagnetic door interlock system by CLP control; liquid fractionation area (16) (4.7 m$^2$) containing: benches (17) with AISI 304 stainless steel coating on 2 levels for material handling and storage; solid fractionation area (18) (4.7 m$^2$) containing: benches (19) with AISI 304 stainless steel coating on 2 levels for material handling and storage, double pass-through 550×550×1100 mm for material input and output with electromagnetic door interlock system by CLP control; engine room (19) containing: fan coil with coarse and fine filtration for air cooling and cleaning, power and control board for electrical supply of the container, automation board of the air conditioning system, interlocking board for doors and pass-throughs.

FIG. 3.1 shows the constructive embodiment of the layout according to the model applied in container (1) in the constructive form of support/labeling/storage area which includes a modular installation of isopanel-coated container or flat partition in sheet steel with thermal and acoustic insulating substrate of polystyrene (EPS) or polyurethane (PUR) or polyisocyanurate (PIR) or rock wool (LDR) or in aluminum wire mesh, the entire interior finished with sanitary rounded profiles (aluminum/PVC/stainless steel or similar) to facilitate cleaning and prevent dirt buildup, vinyl-coated floor with high traffic resistance and resistance against fungi and bacteria, lighting of the rooms will be made through built-in or overlapping luminaires with sealing to the maintenance area, LED lamps, sink drainage system in PVC pipe or similar, sink feeding system in PVC pipe or similar, all doors, displays and accessories in GMP standard, equipped with HVAC system, pressure monitoring, being composed of support area (7.2 m$^2$ or 11.6 m$^2$), said modular installation containing: benches (21) coated with AISI 304 stainless steel (as modulation), the area can be redivided to accommodate the desired modulation, split cooling system for comfort; engine room (22) containing: condenser, power and control board for electrical supply of the container.

Other variants of the modular container units refer to the infusion, diagnosis, surgery, hemodialysis and ICU centers.

All variants being equipped, where appropriate, with a monitoring system connected to information interfaces in connection with external networks to send data and alarms by Internet protocol (IP) for remote management purposes. This monitoring may refer to air pressure, humidity, safety, chemical or biological contamination. The units are validatable or validated through an applicable regulatory agency, with modulations to meet the required environments for ISO8, ISO7, ISO 6, ISO5.

The modules are equipped with a waste control and treatment center according to national or international normative requirements, can be self-sufficient in energy (solar, wind, generator), and have a water collection and treatment center coupled.

The dimensions of the container and its components may also vary according to the application and use, being manufactured in various measures.

Variants of the model presented do not exclude the inclusion of other distinct or additional elements, constructive or configurative variants that contemplate modular units of containers prepared for medical-hospital use, variations that may be applied by those skilled in the art without prejudice to the scope of the invention covered by the following claims.

The invention claimed is:

1. An assembly comprising:
   a container;
   a washing room formed in said container, said working room conforming to an IS07 standard, the washing room having a heating, ventilation and air-conditioning (HVAC) system with a pressure monitor therein;
   a primary antechamber in said container, said primary antechamber having an entrance adapted to allow a person to enter therein, said primary antechamber having an alcohol gel dispenser and a first electromagnetic door interlock system and a cabinet therein, the cabinet adapted to receive supplies therein;
   a gowning antechamber in said container and adapted to allow a patient to change clothes, said gowning antechamber having a sink formed of AISI 304 stainless steel and a faucet positioned over the sink, said gowning antechamber having a second electromagnetic door interlock system therein, said gowning antechamber having a bench positioned therein;
   a storage compartment with a AISI 304 stainless steel coating, said storage compartment adapted to receive a gown therein, said storage compartment positioned in said container;
   a cabinet positioned in said container, said cabinet adapted to store supplies and wastes awaiting disposal;
   a washing and sanitation room formed in said container, said washing and sanitation room having a washing countertop of AISI stainless steel, the washing countertop having a reverse osmosis filter, the reverse osmosis filter adapted to purify water directed to the water inlet, said washer sanitation room having a cabinet adapted to store supplies and to store waste for disposal;
   a double-pass through area positioned in said container and adapted to allow material input and output to and from said container, said double-pass through area having an electromagnetic door interlock system thereon;
   a handling area formed in said container, said handling area having a biosecurity cabin with a workbench, the workbench being formed of an AISI 304 stainless steel; and
   an engine room cooperative with said container, said engine room having a fan coil therein, the fan coil having a filter thereon, the fan coil and filter being adapted for air cooling and cleaning, said engine room having a power and control board therein, the power and control board adapted to supply electrical power to the container, said engine room having an air conditioning system with an automation board therein, said engine room having an interlocking board adapted to control the first and second electromagnetic door interlock systems and said double-pass through area and the reverse osmosis filter.

2. The assembly of claim 1, said container having a floor coated with a vinyl blanket.

3. The assembly of claim 1, wherein said container has partitions formed of sheet steel upon a polystyrene substrate.

4. The assembly of claim 1, wherein said container has partitions having a polyurethane coating.

5. The assembly of claim 1, wherein said container has partitions having a polyisocyanurate coating.

6. The assembly of claim 1, wherein said container has partitions having a rock wool coating.

7. The assembly of claim 1, wherein said container has partitions having an aluminum wire mesh coating.

8. The assembly of claim 1, said container further comprising:
   a monitoring system connected to information interfaces that are connected to external networks, said monitoring system adapted to send data and alarms by Internet protocol, said monitoring system monitoring air pressure, humidity, chemical contamination or biological contamination in said container.

9. The assembly of claim 1, said container further comprising:
   a waste control and treatment center positioned in said container, said waste control and treatment center having an energy system operatively connected thereto.

10. The assembly of claim 1, said container further comprising:
    a support/labeling/storage area defined in said container, said support/labeling/storage area having a plurality of benches each coated with AISI 304 stainless steel.

11. The assembly of claim 1, said container adapted to be used in an infusion center.

12. The assembly of claim 1, said container adapted to be used in a diagnostic center.

13. The assembly of claim 1, said container adapted to be used in a surgery center.

14. The assembly of claim 1, said container adapted to be used in a hematolysis center.

15. The assembly of claim 1, said container adapted to be used in an intensive care unit.

* * * * *